US00PP13443P2

(12) United States Plant Patent
Gerdts et al.

(10) Patent No.: US PP13,443 P2
(45) Date of Patent: Dec. 31, 2002

(54) NECTARINE TREE NAMED 'BURNECTFIVE'

(75) Inventors: Timothy J. Gerdts, Kingsburg, CA (US); John K. Slaughter, Clovis, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/027,832

(22) Filed: Dec. 19, 2001

(51) Int. Cl.[7] ..... A01H 5/00

(52) U.S. Cl. ..... Plt./190

(58) Field of Search ..... Plt./190

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of nectarine tree (*Prunus persica*), and which is denominated varietally as 'Burnectfive' and which produces an attractively colored yellow-fleshed clingstone nectarine which is mature for harvesting and shipment approximately May 15, to May 23 under ecological conditions prevailing in the San Joaquin Valley of Central California.

1 Drawing Sheet

BACKGROUND OF THE NEW VARIETY

Botanical classification: *Prunus persica.*

Variety denomination: 'Burnectfive'.

The present invention relates to a new, novel and distinct variety of nectarine tree, *Prunus persica* var (*nucipersica*), which has been denominated varietally as 'Burnectfive'. The present variety of nectarine tree resulted from an on-going program of fruit and nut tree breeding. The purposes of this program is to improve the commercial quality of deciduous fruit and nut varieties and rootstocks by creating and releasing promising selections of prunus, malus and regia species. To this end we make both controlled and hybrid cross pollinations each year in order to produce seedling populations from which improved progenies are evaluated and selected.

The seedling 'Burnectfive' was originated by us from a population of seedlings grown in our experimental orchards located near Fowler, Calif. The seedlings, grown on their own roots, were the result of an open pollinated cross of the nectarine tree 'Mayfire' (non-patented) which was used as the seed parent. The pollen parent is an unknown nectarine variety. One seedling, which is the present variety, exhibited especially desirable characteristics, and was marked for subsequent observation. After the 1997 growing season, the new, variety was selected for advanced evaluation and repropagation.

ASEXUAL REPRODUCTION

Asexual reproduction of the new and distinct variety of nectarine tree was achieved by budding same to 'Nemaguard' Rootstock (non-patented). This was performed by us in our experimental orchard located near Fowler, Calif. Subsequent evaluations have shown that those asexual reproductions run true to the original tree. All characteristics of the original tree, and its fruit were established, and appeared to be transmitted through succeeding asexual propagations.

SUMMARY OF THE VARIETY

'Burnectfive' is a new and distinct variety of nectarine tree, which is of medium to large size, has vigorous growth, and is a regular and productive bearer of large, firm, yellow flesh, semi-freestone fruit with good flavor and eating quality. The tree has a medium-chilling requirement of approximately 550 hours. The tree also produces relatively uniformly sized fruit throughout the tree, with a high degree of red skin color, and firm flesh. The fruit appears to have good handling and shipping quality. The 'Burnectfive' nectarine tree bears fruit that is ripe for commercial harvesting and shipment on approximately May 15 to May 25 under ecological conditions prevailing in Central California. In comparison to the seed parent 'Mayfire' Nectarine, the new variety ripens about 12 or more days later.

BRIEF DESCRIPTION OF THE DRAWING

The accompanying drawing is a color photograph which depicts a characteristic twig bearing typical leaves; a dorsal view of a single leaf, four whole fruit sufficiently mature for harvesting and shipment; and a fifth fruit which has been cut in half along the suture with the pit being left in one of the halves. The four whole fruit which are shown, beginning from the top right and moving clockwise, illustrate a lateral view showing the suture; a lateral view showing the apex or tip; a lateral view showing the stem; and a lateral view showing the hemisphere opposite the suture. The colors are as nearly true as is reasonably possible in a color photograph of this type. However, due to chemical development, processing and printing, the leaves and fruit depicted in these photographs may or may not be accurate when compared to the actual botanical specimen. For this reason, future color references should be made to the color plates (Royal Horticultural Society) and descriptions provided hereinafter.

DETAILED DESCRIPTION

Referring more specifically to the pomological details of this new and distinct variety of nectarine tree, the following has been observed during the fourth fruiting season under the ecological conditions prevailing at the orchards located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally. — Considered medium large as compared to other common commercial nectarine cultivars ripening in the mid season of maturity. The tree was pruned to a height of approximately 314.8 cm to 386.7 cm at maturity for economic harvesting of fruit.

*Vigor.*—Moderately vigorous. The present variety grew from about 141.0 cm to 195.7 cm in height during the first growing season. The variety was pruned to an approximate height of 106.7 cm during the first dormant season and primary scaffolds were then selected for the desired tree structure.

*Productivity.*—Considered productive. Fruit set varies but is approximately two times or more than the desired crop load. Fruit set is spaced by thinning to develop into the desired market sized fruit. Number of fruit set varies with climatic conditions and prevailing cultural practices during the bloom period.

*Bearer.*—Regular. Fruit set has been heavy, and thinning was necesssary during the past 4 years.

*Form.*—Upright, and pruned to a vase shape.

*Density.*—Medium dense. It has been discovered that pruning the branches from the center of the tree to obtain a vase shape allows for air movement and sunlight to enhance fruit color and renewal of fruiting wood throughout the tree.

*Hardiness.*—The present tree was grown and evaluated in USDA Hardiness Zone 9. Winter chilling requirements are approximately 550 hours below 7.0 degrees C. The variety appears to be hardy under typical Central San Joaquin Valley climatic conditions.

Trunk:

*Diameter.*—Approximately 14.0 cm in diameter when measured at a distance of approximately 15.24 cm above the soil level, at the end of the fifth growing season.

*Bark texture.*—Considered moderately rough, with numerous folds of papery scarfskin being present.

*Lenticels.*—Numerous flat, oval lenticels present. The lenticels range in size in size from approximately 2.0 to 5.0 millimeters in width, and from 1 to 2 millimeters in height.

*Lenticel color.*—Considered an Orange Brown. (RHS Greyed-Orange N172 A). Bark Coloration — Variable, but it is generally considered to be a grey-brown (RHS Greyed-Orange Group 177 A).

Branches:

*Size.*—Considered medium for the variety.

*Diameter.*—Average as compared to other varieties. The branches have a diameter of about 72.0 millimeters when measured during the fourth year after grafting.

*Surface texture.*—Average, and appearing furrowed on wood which is several years old.

*Crotch angles.*—Primary branches considered variable between about 45 to 49 degrees from the horizontal axis. This characteristic is not distinctive of the variety, however.

*Current season shoots.*—Surface texture — Substantially glabrous.

*Internode length.*—Approximately 2.3 to 2.4 cm.

*Color of mature branches.*—Medium brown, (RHS Grey Brown Group N199C).

*Current seasons shoots.*—Color. — Light green, (RHS Green Group 143 A). The color of new shoot tips is considered as a bright and shiny green (RHS Green Group 134 B).

Leaves:

*Size.*—Considered medium for the species. Leaf measurements have been taken from vigorous upright current season growth at approximately mid-shoot.

*Leaf length.*—Approximately 150 to 165 millimeters.

*Leaf width.*—Approximately 35 to 40 millimeters.

*Leaf base shape.*—Slightly oblique relative to the leaf longitudinal axis.

*Leaf form.*—Lanceolate.

*Leaf tip form.*—Acuminate.

*Leaf color.*—Dark green, (RHS Green Group 137 A).

*Leaf texture.*—Glabrous.

*Lower surface.*—Medium green, (RHS Green Group 137 D).

*Leaf venation.*—Pinnately veined.

*Mid-ivein.*—Color. — Light yellow green, (RHS Yellow Green Group 144 B).

*Leaf margins.*—Slightly undulating.

*Form.*—Considered crenate, occasionally doubly crenate.

*Uniformity.*—Considered generally uniform.

*Leaf petioles.*—Size. — Considered medium long to long. Length. — 9.0 to about 12.0 mm. Diameter. — 1.5 to about 2.5 mm. Color. — Pale green, (RHS Yellow Green Group 144 D).

*Leaf glands.*—Size. — 1.0 mm in height and about 1.0 to 2.0 mm in width. Numbers. — Generally one per side, occasionally two per side. Type. — Reniform, and considered reasonably unappressed to the petiole margin. Color. — Greenish brown (RHS Yellow Green Group144 B).

*Leaf stipules.*—Size. — Medium large for the variety. Number. — Typically 2 per leaf bud, and up to 6 per shoot tip. Form. — Lanceolate in form and having a serrated margin. Color. — Green (RHS Green Group 132 A) when young, but graduating to a yellow-brown color (RHS Grey Orange group 177 A) with advancing senescence. The stipules are considered to be early deciduous.

Flowers:

*Flower buds.*—Generally — The floral buds are considered to be large, 15 millimeters wide and 21 millimeters long; conic in form; and slightly appressed relative to the bearing shoot.

*Flower buds.*—Color — The bud scales are gray-brown, (approximately RHS Greyed Purple Group 183 A). The buds are considered hardy under typical central San Joaquin Valley climatic conditions.

*Hardiness.*—No winter injury has been noted during the last several years of evaluation in the Central San Joaquin Valley. The current variety has not been intentionally subjected to drought or heat stress and therefore this information is not available.

*Date of first bloom.*—Feb. 22, 2000.

*Blooming time.*—Considered early in relative comparison to other commercial nectarine cultivars growing in the Central San Joaquin Valley. The date of full bloom was observed on Mar. 2, 2000. Date of bloom varies slightly with climatic conditions.

*Duration of bloom.*—Approximately 8 days. Varies slightly with climatic conditions.

*Flower type.*—The variety is considered to have a showy type flower.

*Flower size.*—Flower diameter at full blom is approximately 31.0 to 36.0 millimeters.

*Bloom quantity.*—Considered abundant.

*Flower bud frequency.*—Normally 1 to 2 appear per node.

*Petal size.*—Generally — Considered medium large to large for the species. Length. — Approximately 16.0 to 19.0 millimeters. Width. — Approximately 17.0 to 19.0 millimeters.

*Petal form.*—Broadly ovate.

*Petal count.*—Nearly always 5.

*Petal texture.*—Glabrous.

*Petal color.*—Light pink when young, (RHS Red Purple Group 65 B), and darkening with advancing senescence and exposure to sunlight to a medium to dark pink (RHS Red Purple Group 65 A).

*Fragrance.*—Slight.

*Petal claw.*—Form. — The claw is considered truncate and has a medium-large size when compared to other varieties. Length. — Approximately 8.0 to 10.0 millimeters. Width. — Approximately 6.0 to 8.0 millimeters.

*Petal margins.*—Generally considered variable, from nearly smooth, to moderately undulate and ruffled, especially apically.

*Petal apex.*—Generally — The petal apices appear slightly domed.

*Flower pedicel.*—Length. — Considered medium-long, and having an average length of approximately 3.0 to 5.0 millimeters. Diameter. — Considered average, approximately 2.0 millimeters. Color. — A medium Green (RHS — Grey Brown Group N199 D).

*Floral nectaries.*—Color. — A dull orange-gold (RHS Greyed Red Group 178 B).

*Calyx.*—Surface Texture. — Generally glabrous. Color. — A dull red, (approximately RHS Greyed Purple Group 183 A).

*Sepals.*—Surface texture. — The surface has a short, fine, wooly and sparse texture. Size. — Average, and ovate in form. Color. — A dull red, (approximately RHS Greyed-Red Group 178 A).

*Anthers.*—Generally. — Average to above average in length. Color. — Red to reddish-orange dorsally, (approximately RHS Greyed Purple Group 179 A).

*Pollen production.*—Pollen is abundant, and has a yellow color, (approximately RHS Yellow Orange Group 17 B).

*Filaments.*—Size. — Variable in length, approximately 11.0 to 13.0 millimeters in length. Color. — White, (RHS Red Purple Group 62 D).

*Pistil.*—Number. — Usually 1, rarely 2. Generally. — Average in size. Length. — Approximately 14.0 to 16.0 millimeters including the ovary. Color. — Considered a very pale green, (approximately RHS Yellow Green Group 151 D). Surface Texture — glabrous.

Fruit:

*Maturity when described.*—Firm ripe condition (shipping ripe); Date of first picking, — May 15, 2000; Date of last picking, — May 23, 2000. The date of harvest varies slightly with climatic conditions.

*Size.*—Generally — Medium large, and considered uniform.

*Average cheek diameter.*—Approximately 73.0 to 75.0 millimeters.

*Average axial diameter.*—Approximately 71.0 to 73.0 millimeters.

*Typical weight.*—Approximately 231.0 grams. This is highly dependent on cultural practices and is therefore not distinctive of the variety.

*Fruit form.*—Generally — Moderately oblate. The fruit is generally uniform in symmetry.

*Fruit suture.*—Shallow, occasionally lipped, and which extends from the base to the apex. No apparent callousing or stitching exists along the suture line.

*Suture.*—Color — This appears to be a yellow to golden yellow background color, (approximately RHS Yellow Orange Group 26 B) and further having some red orange coloration (approximately RHS Red Group 46 B).

*Ventral surface.*—Form — Slightly indented.

*Apex.*—Rounded.

*Base.*—Retuse.

*Stem cavity.*—Rounded to slightly elongated in the suture plane. Average depth of the stem cavity is about 1.15 cm. Average width is about 2.31 cm.

*Fruit skin.*—Thickness. — Considered medium in thickness, and tenacious to the flesh. Texture. — Glabrous. Taste. — Non-astringent. Tendency to crack. — None observed.

*Fruit skin color.*—Blush Color. — The blush color is a variable dark red, (approximately RHS Red Group 46 A to 45 B). Ground Color. — Yellow orange (approximately RHS Yellow Orange Group 26 B).

*Fruit stem.*—Medium in length, approximately 7.0 to 8.0 millimeters. Diameter. — Approximately 2.0 to 3.0 millimeters. Color. — Pale yellow-green (approximately RHS Yellow Green Group 145 B).

*Flesh.*—Ripens. — Evenly. Texture. — Firm and dense. Fibers. — Few, small and tender. Aroma. — Very slight. Eating quality. — Very good. Flavor. — Considered sweet and mildly acidic. The flavor is considered both pleasant and balanced. Juice. — Moderate. Brix. — 12.0 degrees. Varies slightly with the number of fruit per tree, prevailing cultural practices and surrounding climatic conditions. Flesh color. — Pale yellow, (approximately RHS Yellow Orange Group 20 A).

Stone:

*Type.*—Clingstone.

*Size.*—Considered medium for the variety.

*Length.*—Average, about 22.0 to 24.0 millimeters.

*Width.*—Average, about 21.0 to 22.0 millimeters.

*Diameter.*—Average, about 18.0 to 19.0 millimeters.

*Form.*—Obovoid.

*Base.*—The stone is usually rounded, but may vary from rounded to straight.

*Apex.*—Shape. — The stone apex is raised and has an acute, short tip.

*Stone surface.*—Surface Texture — Irregularly furrowed toward the apex; and pitted toward the base. The stone exhibits substantial pitting laterally. Substantial grooving over the apical shoulders is evident. Surface pitting is prominent generally, and more frequently, it is present basally. Ridges. — Surface texture varies from sharp to rounded. Ventral Edge. — Width — Considered medium, and having a dimension of approximately 4.0 to 5.0 millimeters at approximately mid-suture. The wings are most prominent over the basal area. Dorsal Edge. — Shape. — Full, heavily grooved, and having jagged edges. The dorsal edge is moderately eroded over the apical shoulder.

*Stone color.*—The color of the dry stone is a light straw colored yellow, (approximately RHS Yellow Orange Group 18 C.)

*Tendency to split.*—Few but very infrequent splitting noted.

*Kernel.*—Size. — Length — 17.0 mm.; Width — 12.0 mm.; Thickness — 3.0 millimeters. Form. — Obovoid. Pellicle. — Pubescent. Color. — (RHS Orange White 159 C). The kernel and its embryo are immature at the time of fruit maturity.

*Use.*—The subject variety 'Burnectfive' is considered to be a Nectarine of the early-season maturity, and which produces fruit which are very firm, attractively colored, and which are useful for both local and long distance shipping.

*Keeping quality.*—Excellent. Fruit has stored well up to 21 days after harvest at 1.0 degree Celsius.

*Shipping quality.*—Good. Fruit showed minimal bruising of the flesh or skin damage after normal harvest and packing procedures.

*Resistance to insects and disease.*—No particular susceptibilities were noted. The present variety has not been tested to detect for any susceptibilities or resistances to any known plant and/or fruit diseases.

Although the new variety of nectarine tree possesses the described characteristics when grown under the ecological conditions prevailing near Fowler, Calif., in the Central part of the San Joaquin Valley of California, it will be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new and distinct variety of nectarine tree, substantially as illustrated and described, and which is characterized principally as to novelty by producing an attractively colored yellow-fleshed clingstone nectarine which is mature for harvesting and shipment approximately May 15 to May 23 under the ecological conditions prevailing in the San Joaquin Valley of Central California.

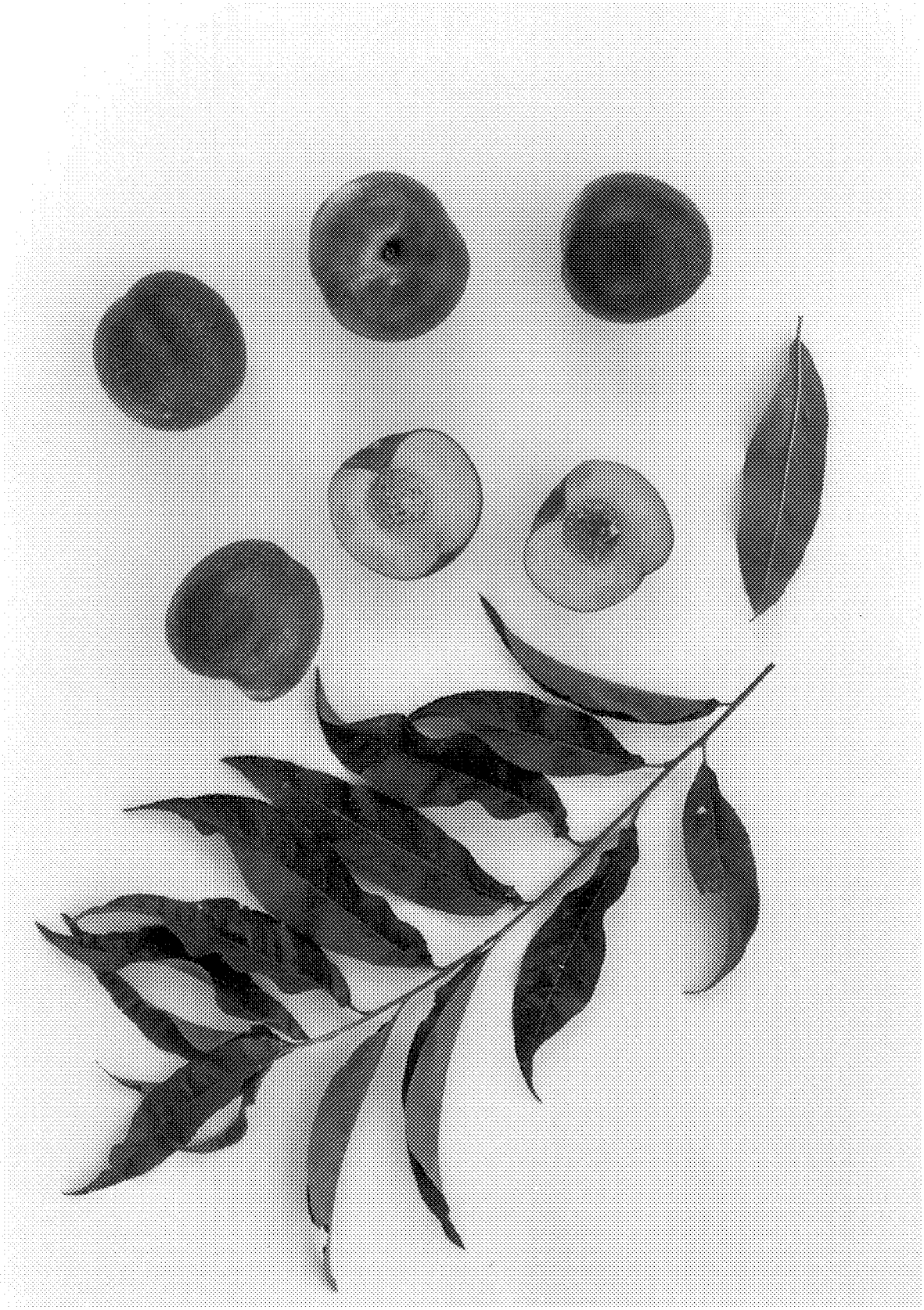

* * * * *